(12) United States Patent  
Black

(10) Patent No.: US 8,876,871 B2  
(45) Date of Patent: Nov. 4, 2014

(54) TRANSVERSE CONNECTOR

(71) Applicant: Globus Medical, Inc., Audubon, PA (US)

(72) Inventor: Michael Black, Swarthmore, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 14/037,899

(22) Filed: Sep. 26, 2013

(65) Prior Publication Data

US 2014/0031875 A1  Jan. 30, 2014

Related U.S. Application Data

(63) Continuation of application No. 12/877,667, filed on Sep. 8, 2010, now Pat. No. 8,568,456.

(60) Provisional application No. 61/244,156, filed on Sep. 21, 2009.

(51) Int. Cl.  
  *A61B 17/70* (2006.01)

(52) U.S. Cl.  
  CPC .................................. *A61B 17/7049* (2013.01)  
  USPC ............................................ 606/279; 606/250

(58) Field of Classification Search  
  CPC ........... A61B 17/7049; A61B 17/7052; A61B 17/705  
  USPC ........................................ 606/250–278, 279  
  See application file for complete search history.

(56) References Cited

U.S. PATENT DOCUMENTS

| | | | |
|---|---|---|---|
| 7,628,799 B2 * | 12/2009 | Richelsoph et al. | 606/250 |
| 8,568,456 B2 * | 10/2013 | Black | 606/250 |
| 2003/0045874 A1 * | 3/2003 | Thomas, Jr. | 606/61 |
| 2003/0114852 A1 * | 6/2003 | Biedermann et al. | 606/61 |
| 2005/0149019 A1 * | 7/2005 | Sasing et al. | 606/61 |
| 2006/0009766 A1 * | 1/2006 | Lee et al. | 606/61 |
| 2006/0229616 A1 * | 10/2006 | Albert et al. | 606/61 |

* cited by examiner

*Primary Examiner* — Jan Christopher Merene

(57) ABSTRACT

A transverse connector system having a first and a second locking element. The present invention also provides transverse rod having opposing first and second ends, the first end being retained within a portion of the first locking element and the second end being retained within a portion of the second locking element. The first locking element is configured with a connector body for engaging and capturing an elongated rod and a transverse rod simultaneously.

8 Claims, 2 Drawing Sheets

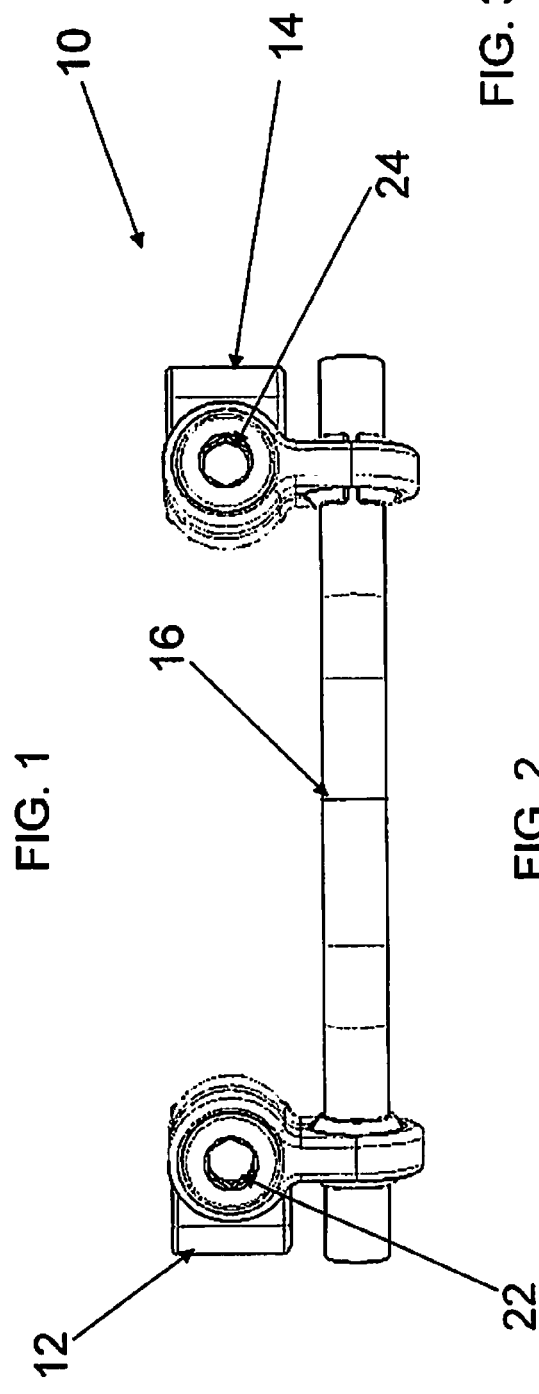
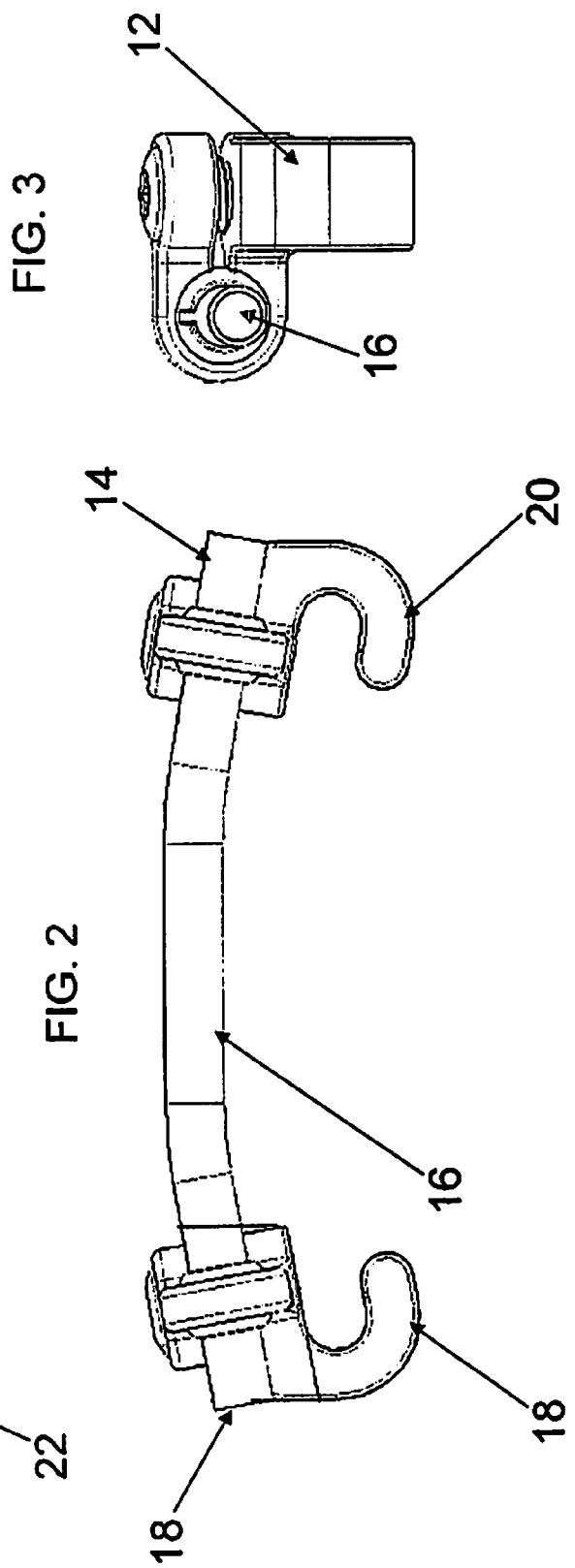
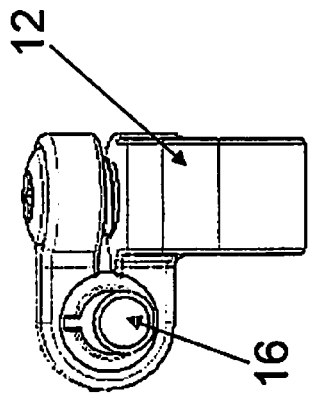

TRANSVERSE CONNECTOR

CROSS-REFERENCE TO RELATED APPLICATIONS

The present application is a continuation application of U.S. patent application Ser. No. 12/877,667 filed on Sep. 8, 2010, now U.S. Pat. No. 8,568,456 which claims priority to U.S. Provisional Application 61/244,156 filed on Sep. 21, 2009. All publications and patent applications mentioned in this specification are herein incorporated by reference to the same extent as if each individual publication or patent application was specifically and individually indicated to be incorporated by reference.

FIELD OF THE INVENTION

The present invention is generally directed for use in stabilizing the spine. In particular, the present invention is directed to a device that provides additional support for a posterior stabilization system.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, an anchoring member such as a pedicle screw along with a vertical solid member can help restore spinal elements to a pain free situation, or at least may help reduce pain or prevent further injury to the spine.

There is a need for a transverse connector that connects two rod systems that are positioned on opposing sides of the spine. There is also a need for a transverse connector that provides stability to the spinal implant construct as well as being smaller in profile so as not to interfere with adjacent screw or the spinal cord.

SUMMARY OF THE INVENTION

The present invention provides a transverse connector having a first and a second locking element and a transverse rod having opposing first and second ends, the first end being retained within a portion of the first locking element and the second end being retained within a portion of the second locking element. The first locking element and the second locking element include a connector body for engaging and capturing an elongated rod and a transverse rod simultaneously. The connector bodies of the first and second locking elements comprise a clamping element and a hook element, the hook element having at least one deformable protrusion for retaining and capturing an elongated rod and providing audible and tactile feedback when the elongated is positioned in the hook element.

BRIEF DESCRIPTION OF THE DRAWINGS

The attached drawings illustrate the elements of the present invention. Design and utility features of the present invention are also disclosed.

FIG. 1 is a to view of one embodiment of a transverse connector according to the present invention;

FIG. 2 is a front view of a transverse connector system according to the present invention;

FIG. 3 is a side view of the transverse connector according to the present invention.

DETAILED DESCRIPTION OF THE INVENTION

Figure 4:
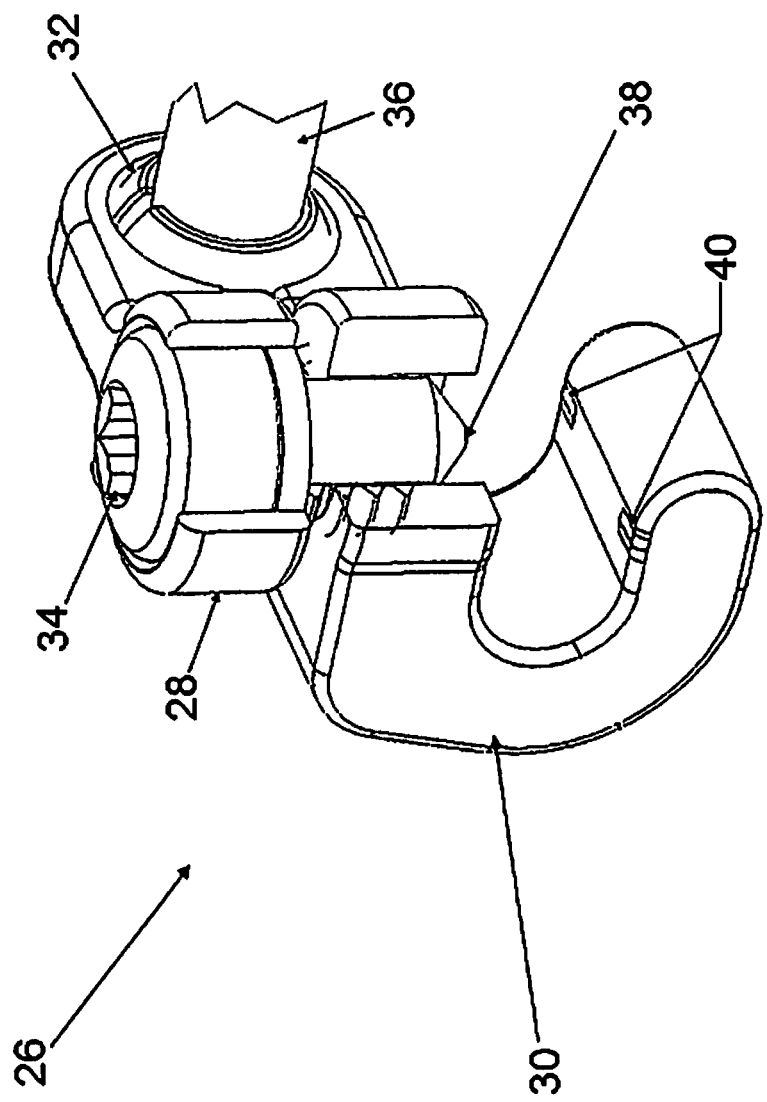
FIG. 4 illustrates a perspective view of the locking element according to the present invention.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to limit the scope of the disclosure, including the claims, is limited to that embodiment.

Referring now to FIGS. 1, 2, and 3, a low profile transverse connector 10 according to the present invention is illustrated. The transverse connector 10 provides additional stability and support for a posterior stabilization system. Transverse connector 10 is generally positioned between the spinous processes of the vertebrae and coupled to elongated rods that connect to adjacent vertebrae. The engaging and capturing of the transverse connector 10 to the elongated rods will be discussed in greater detail with reference to FIG. 4

The transverse connector 10 is comprised of locking elements 12, 14 which are coupled to each other through a transverse rod 16. Each locking element 12, 14 is provided with hook elements 18, 20 and a set screw assembly 22, 24. As illustrated in FIGS. 1-3, transverse rod 16 is captured and retained by each of the locking elements 12, 14. These features will be discussed in greater detail with reference to FIG. 4.

Now turning to FIG. 4, the features of the first and second locking elements 12 and 14 are illustrated in detail. Since each of the locking elements 12, 14 are substantially similar, the elements and functions of a single locking element 26 will be described in greater detail for clarity and ease of understand. The locking element 26 is comprised of a connector body 28, a hook element 30, a bushing 32, and a locking set screw 34. The components of the locking element 26 are configured and dimensioned to capture and retain a transverse rod 36 and an elongated rod by utilizing the locking set screw 34.

The locking element 26 is also comprised of a connector body 28 that acts as a clamping element, which is configured with a screw hole that extends through the connector body 28. The connector body 28 configured to form a c-clamp containing a spherical collet 32. The c-clamp is configured to retain and capture a transverse rod 36 as illustrated in FIG. 4. When a fastener 34 is advanced within the screw hole of the clamping element, the pressure is applied to the spherical collet 32 thereby capturing the transverse rod 36 which is positioned within the c-clamp. When the fastener 34 is not advanced the transverse rod 36 is able to move in any angle and can be moved laterally since there is no pressure applied to the clamping element.

As illustrated in FIG. 4, the spherical collet 32 is positioned within the c-clamp. The spherical collet 32 forms a collar around the transverse rod 36 and exerts a strong clamping force on the object when it is tightened. When pressure is not applied upon the spherical collet 32, the transverse rod 36 is able to rotate in any angle and can be translated in laterally. It should be noted that collets can range in holding capacity from zero to several inches in diameter. The most common type of collet is one that grips a round bar or tool, but there are collets for square, hexagonal, and other shapes.

The locking element 26 also comprises a screw 34 that may be used in one particular embodiment of the present invention. The screw 34 is a fastening means that is used to fasten the clamping element as well as retain the elongated rod within the hook element 30. The screw 34 is generally threaded and is adapted to be received by the screw hole on the top portion of the base element 28. Any type of screw that facilitates the fastening of the clamping element may be used in the invention. The screw 34 in one particular embodiment can be provided with threads along its elongated shaft. In order to aid in tightening the screw 34, the screw 34 may include projections with a curved surface to aid in gripping the screw. The length of the elongate shaft may be varied depending on the size and configuration of the locking element 26. As the screw 34 is turned and advanced into the screw hole, the clamping element is tightened thereby retaining and capturing the transverse rod 36 in one specific angle and position. Simultaneously, as the screw 34 is advanced through the use of a screw driver, the tip 38 of the screw 34 is advanced vertically and applies pressure upon an elongated rod. The elongated rod is retained within hook element 30 through the pressure applied by the screw 34. The hook element 30 is also provided with protrusions 40 which enable the elongated rod to be retained within the curvature of the hook element 34. The protrusions 40 provide an audible and tactile feedback when the elongated rod is positioned within the hook element 30. As a result of the screw 34 and the hook element 30, the elongated rod is captured and retained in a tight position between the curved edge of the hook element 30 and the protrusions 40. It should be noted that the present invention is not limited to a screw 34 as a fastening means. Any type of fastening device which applied pressure upon the clamping element and simultaneously applied pressure upon elongated rod would be compatible with the present invention.

It should be further noted that each locking element is fastened separate from the other. For instance, each of the locking elements are fastened separately to secure a portion of the transverse rod and the corresponding elongated rod. There are several major benefits of the invention for use in the human spine. The transverse connector enables a single step locking mechanism, which allows the surgeon to lock the construct with a single fastener, reducing surgery times. Second is the large amount of flexibility that is afforded to the surgeon in angular as well as linear adjustment. Because of the poly-axial connection between the locking elements and the connecting rod, either end can be translated along the rod to account for rod spacing and can be adjusted to any angle necessary. Another benefit is the top loading nature of the present invention, which enables a surgeon easy access for insertion and locking.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A method for stabilizing spinal elements comprising the steps of:
   accessing posterior elements of the spine;
   positioning a transverse connector between adjacent spinous processes;
   wherein the transverse connector comprises:
      a first and a second locking element; and
      a transverse rod having opposing first and second ends, the first end being retained within a portion of the first locking element and the second end being retained within a portion of the second locking element;
      wherein the first locking element includes a connector body for engaging and capturing an elongated rod and the transverse rod simultaneously, wherein the connector body includes a clamping element and a spherical collet independent from the clamping element, wherein the clamping element receives the spherical collet therein,
      wherein the clamping element is a c-clamp having opposing ends and the spherical collet is positioned within the c-clamp and wherein the transverse rod can be translated and articulated in a plurality of multiple angles,
      wherein the connector body comprises a screw hole for receiving a screw, wherein as the screw is advanced through the screw hole, the opposing ends of the c-clamp are brought closer together to tighten the clamping element in order to capture the transverse rod and a distal tip of the screw applies pressure via direct contact to the elongated rod.

2. The method of claim 1, wherein the transverse rod is curved.

3. The method of claim 1, wherein the connecting body further comprises a hooking element having multiple protrusions configure to deform for capturing the elongated rod and providing tactile and audile feedback.

4. The method of claim 1, wherein the second locking element has a second connector body for capturing and retaining a second elongated rod and the transverse rod simultaneously.

5. A method for stabilizing spinal elements comprising the steps of:
   accessing the posterior elements of the spine;
   connecting a transverse connector to a first and second elongated rod;
   wherein the transverse connector comprises:
      a first and a second locking element;
      a transverse rod having opposing first and second ends, the first end being retained within a portion of the first locking element and the second end being retained within a portion of the second locking element;
      wherein the first locking element and the second locking element comprise a connector body for engaging and capturing a first and second elongated rod respectfully and the transverse rod simultaneously, wherein the first locking element engages and captures the first elongated rod and the second locking element engages and captures the second elongated rod,
      wherein the connector bodies of the first and second locking elements comprise a clamping element, a spherical collet independent from the clamping element and a hook element, the hook element having at least one deformable protrusion for retaining and capturing the first and second elongate rod and providing audible and tactile feedback when the first and second elongated rod is positioned in the hook element, wherein the clamping element receives the spherical collet therein, wherein the clamping element is a c-clamp and the spherical collet is positioned within the c-clamp and wherein the transverse rod can be translated and articulated in a plurality of multiple angles, wherein each of the connector bodies comprises a screw hole for receiving a screw, wherein as the screw is advanced through the screw hole, opposing ends of each of the clamping elements are brought closer together to tighten each clamping element in order to capture the transverse rod and a distal tip of the screw applies pressure via direct contact to the elongated rod.

6. The method according to claim 5, wherein when the screw is advanced in the screw hole, the clamping element is tightened to capture a cross connecting rod and the tip of the screw captures the elongated rod simultaneously.

7. The method according to claim 5, wherein the transverse rod is securable in a plurality of multiple angles by the locking element.

8. A method for stabilizing spinal elements comprising the steps of:
accessing posterior elements of the spine;
positioning a transverse connector between adjacent spinous processes;
wherein the transverse connector comprises:
a first and a second locking element; and
a transverse rod having opposing first and second ends, the first end being retained within a portion of the first locking element and the second end being retained within a portion of the second locking element;
wherein the first locking element includes a connector body for engaging and capturing an elongated rod and the transverse rod simultaneously, wherein the connector body includes a clamping element and a spherical collet independent from the clamping element, wherein the clamping element receives the spherical collet therein,
wherein the clamping element has opposing ends and the spherical collet is positioned within the clamp and wherein the transverse rod can be translated and articulated in a plurality of multiple angles,
wherein the connector body comprises a screw hole for receiving a screw, wherein as the screw is advanced through the screw hole
wherein when the screw is advanced in the screw hole, the tip of the screw captures the elongated rod and the clamping element is tightened to capture a cross connecting rod simultaneously.

* * * * *